US011602521B2

United States Patent
Rao et al.

(10) Patent No.: US 11,602,521 B2
(45) Date of Patent: Mar. 14, 2023

(54) N,N-DIMETHYLTRYPTAMINE COMPOSITIONS AND METHODS

(71) Applicant: ATAI Life Sciences AG, Berlin (DE)

(72) Inventors: Srinivas G. Rao, Encinitas, CA (US); Glenn Short, Scituate, MA (US)

(73) Assignee: ATAI LIFE SCIENCES AG, Berlin (DE)

(*) Notice: Subject to any disclaimer, the term of this patent is extended or adjusted under 35 U.S.C. 154(b) by 0 days.

(21) Appl. No.: 17/730,013

(22) Filed: Apr. 26, 2022

(65) Prior Publication Data

US 2022/0339139 A1    Oct. 27, 2022

Related U.S. Application Data

(60) Provisional application No. 63/179,679, filed on Apr. 26, 2021.

(51) Int. Cl.
*A61K 31/4045* (2006.01)
*A61K 9/00* (2006.01)

(52) U.S. Cl.
CPC .......... *A61K 31/4045* (2013.01); *A61K 9/006* (2013.01); *A61K 9/0014* (2013.01)

(58) Field of Classification Search
CPC .............. A61K 31/4045; A61K 9/0014; A61K 9/006
USPC ....................................................... 514/415
See application file for complete search history.

(56) References Cited

U.S. PATENT DOCUMENTS

2020/0390746 A1* 12/2020 Rands ................. C07D 209/16
2020/0397752 A1   12/2020 Perez Castillo et al.
2021/0346347 A1   11/2021 Witowski et al.
2021/0378969 A1   12/2021 Rands et al.
2022/0031662 A1    2/2022 Terwey
2022/0071958 A1    3/2022 Terwey
2022/0079881 A1    3/2022 Modi
2022/0304980 A1    9/2022 Arnold et al.

FOREIGN PATENT DOCUMENTS

WO    2022061242 A1    3/2022

OTHER PUBLICATIONS

Strassman, Dose-Response Study of N,N-Dimethyltryptamine, in HumansArchives of General Psychiatry • Mar. 1994. p. 85-97) (Year: 1994).*
Ruiz et al, Routes of Drug Administration: Dosage, Design, and Pharmacotherapy Success, Routes of Drug Administration, Chapter 6, Jan. 2018, 1-43 (Year: 2018).*
Berge et al, Pharmaceutical Salts, Journal of Pharmaceutical Science, Jan. 1977, p. 1-19) (Year: 1977).*

* cited by examiner

*Primary Examiner* — Taylor V Oh
(74) *Attorney, Agent, or Firm* — Jeff B. Vockrodt; Culhane Meadows, PLLC (57) ABSTRACT

A composition including N,N-dimethyltryptamine (DMT) or a pharmaceutically acceptable salt thereof capable of exhibiting a therapeutically effective blood level of DMT from between about 20 and about 60 minutes when administered to a human. A method of treating a neurological disease or condition comprising administering buccally, sublingually, subcutaneously or intranasally to a subject in need thereof an effective amount of DMT or a pharmaceutically acceptable salt thereof, capable of exhibiting a therapeutically effective level of DMT from for between about 20 to about 60 minutes when administered to a human.

27 Claims, 5 Drawing Sheets

Serum concentration of DMT over time following administration of a formulation comprising 50 mg DMT succinate

| Time | 0 | 5 | 10 | 15 | 20 | 25 | 30 | 35 | 40 | 45 | 50 | 55 | 60 | 65 | 70 | 75 | 80 | 85 | 90 | 95 | 100 |
|---|---|---|---|---|---|---|---|---|---|---|---|---|---|---|---|---|---|---|---|---|---|
| Composition Concentration | 100% | 61% | 37% | 23% | 14% | 8% | 5% | 3% | 2% | 1% | 1% | 0% | 0% | 0% | 0% | 0% | 0% | 0% | 0% | 0% | 0% |
| Drug Release (%) | 30.0% | 20.0% | 15.0% | 15.0% | 15.0% | 5.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| Drug Release (mg) | 5.86 | 7.48 | 7.49 | 7.49 | 7.49 | 5.54 | 3.38 | 2.06 | 1.26 | 0.77 | 0.47 | 0.28 | 0.17 | 0.11 | 0.06 | 0.04 | 0.02 | 0.01 | 0.01 | 0.01 | 0.00 |
| Serum Concentration (nmol/L) | 251.3 | 320.7 | 321.1 | 321.4 | 321.6 | 238.0 | 145.0 | 88.4 | 53.9 | 32.8 | 20.0 | 12.2 | 7.4 | 4.6 | 2.8 | 1.7 | 1.0 | 0.6 | 0.4 | 0.2 | 0.1 |

| Time | 0 | 5 | 10 | 15 | 20 | 25 | 30 | 35 | 40 | 45 | 50 | 55 | 60 | 65 | 70 | 75 | 80 | 85 | 90 | 95 | 100 |
|---|---|---|---|---|---|---|---|---|---|---|---|---|---|---|---|---|---|---|---|---|---|
| Composition Concentration | 100% | 61% | 37% | 23% | 14% | 8% | 5% | 3% | 2% | 1% | 1% | 0% | 0% | 0% | 0% | 0% | 0% | 0% | 0% | 0% | 0% |
| Drug Release (%) | 15% | 20.0% | 20.0% | 15.0% | 15.0% | 10.0% | 5.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| Drug Release (mg) | 2.9 | 5.7 | 7.4 | 7.4 | 7.5 | 6.5 | 4.9 | 3 | 1.8 | 1.1 | 0.7 | 0.4 | 0.3 | 0.2 | 0.1 | 0.1 | 0 | 0 | 0 | 0 | 0 |
| Serum Concentration (nmol/L) | 125.66 | 244.14 | 316.35 | 318.48 | 319.78 | 278.68 | 211.74 | 129.06 | 78.66 | 47.95 | 29.22 | 17.81 | 10.86 | 6.61 | 4.03 | 2.46 | 1.50 | 0.91 | 0.56 | 0.34 | 0.20 |

FIGURE 1

DMT % release profiles which maximize the time at which DMT serum concentrations are maintained at therapeutically relevant concentrations

| Time | 0 | 5 | 10 | 15 | 20 | 25 | 30 | 35 | 40 | 45 | 50 | 55 | 60 | 65 | 70 | 75 | 80 | 85 | 90 | 95 | 100 |
|---|---|---|---|---|---|---|---|---|---|---|---|---|---|---|---|---|---|---|---|---|---|
| Formulation 1 (T₁₂ ~7 minutes) | 15.0% | 30.0% | 30.0% | 20.0% | 5.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| Formulation 2 (T₁₂ ~7 minutes) | 15.0% | 20.0% | 20.0% | 15.0% | 15.0% | 10.0% | 5.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| Formulation 3 (T₁₂ ~7 minutes) | 15.0% | 25.0% | 25.0% | 10.0% | 10.0% | 10.0% | 5.0% | 0.0% | 0.0% | 0.0% | 0.0% | 0.0% | 0.0% | 0.0% | 0.0% | 0.0% | 0.0% | 0.0% | 0.0% | 0.0% | 0.0% |

FIGURE 2

FIGURE 3a. DMT permeation through pig buccal mucosa measured in a Franz cell (mean of three replicates, error bars indicate standard deviation)

FIGURE 3b. DMT permeation through pig buccal mucosa measured in a Franz cell (data shown for three replicates)

FIGURE 4

Components of a Franz Diffusion Cell

FIGURE 5

N,N-DIMETHYLTRYPTAMINE COMPOSITIONS AND METHODS

CROSS-REFERENCE TO RELATED APPLICATIONS

The present application claims priority to, and the benefit of, U.S. Provisional Patent Application No. 63/179,679, filed Apr. 26, 2021, the entire contents of which are incorporated herein by reference in its entirety for all purposes.

FIELD OF THE INVENTION

The present disclosure relates to novel N,N-dimethyltryptamine ("DMT") compositions and methods of treating neurological diseases and conditions. Specifically, the disclosure provides improved pharmaceutical compositions comprising N,N-dimethyltryptamine or a pharmaceutically acceptable salt thereof for the treatment of neurological diseases and conditions.

BACKGROUND OF THE INVENTION

Lysergic acid diethylamide ("LSD"), psilocybin and N,N-dimethyltryptamine are serotonergic agents often referred to as "classical hallucinogens" or "psychedelics," and have the ability to induce qualitatively altered states of consciousness, such as euphoria, trance, transcendence of time and space, spiritual experiences, or dissolution of self-boundaries, while other effects such as sedation, narcosis, or excessive stimulation are only minimal. Chemically, serotonergic psychedelics are either phenylalkylamines or indoleamines, with the indoleamine class being divided into two subsets, ergolines and tryptamines.

Naturally occurring psychedelics, such as the N,N-dimethyltryptamine, which is contained in the South American shrub *Psychotria viridis*, psilocybin, which is contained in over 200 mushroom species, or mescaline, which is contained in the Peyote cactus of the American Southwest and Northern Mexico, have been used for centuries by indigenous cultures in ritualistic or sociocultural contexts, and in the context of religious sacraments. While an unspecific "healing" potential had been ascribed to the use of naturally occurring psychedelics in those settings, more scientific investigations into their potential therapeutic application for defined diseases had not been pursued until after the discovery of the synthetic ergoline lysergic acid diethylamide ("LSD") in 1943.

With emerging knowledge about the serotonin system and its role in brain function, researchers began to specify the molecular activity of psychedelic drugs. However, how that activity translated into the observed therapeutic effects in mental disorders was less clear. Two main concepts were proposed: The first concept was coined "psycholytic therapy" and it emphasized the ability of psychedelics given at low doses to facilitate the loosening of psychological defensive mechanisms, which in combination with psychotherapy allows a deep introspective insight and the revival of traumata and their subsequent catharsis. The basic mechanism considered in the psycholytic approach was therefore the activation and deepening of the concomitant psychotherapeutic process, and it required multiple drug and therapy sessions. The second concept was coined as "psychedelic therapy" and it emphasized the ability of psychedelics given at relatively high single doses to induce so called "peak psychedelic experiences." Peak experiences are predominantly characterized by the loss of judgment to time and space and the dissolution of ego boundaries, which often culminates in the experience of a blissful state and feelings of being a whole and harmonious existence in the cosmic unity. The basic mechanism considered in the psychedelic approach was therefore to produce a unique, overwhelming experience with an intuitive perception of psychological integration and harmony and subsequent self-improvements and enhanced joy in living and a sense of inner peace.

Although scientific research around the use of psychedelics for the treatment of mental disorders blossomed in the 1960s, there was also a rapidly growing recreational use of these substances, and soon psychedelics were depicted in the media as highly dangerous drugs of abuse. A perceived danger to the social order led to the passage of the United States Controlled Substances Act of 1970, under which LSD and other psychedelics were placed into the most restrictive category Schedule 1, which contains drugs deemed to have no medical use and a high potential for abuse. Very little progress was made regarding possible therapeutic uses of psychedelic drugs for the next 30 years.

Recently, interest in the field of psychedelic therapy has resurged, and classical psychedelics have shown preclinical and clinical promise in treating psychiatric disorders (Carhart-Harris and Goodwin, *The Therapeutic Potential of Psychedelic Drugs: Past, Present and Future, Neuropsychopharmacology;* 42, 2105-2113 (2017)). In particular, psilocybin has demonstrated significant improvement in a range of depression and anxiety rating scales in randomized double-blind studies (Griffiths et al., *Psilocybin produces substantial and sustained decreases in depression and anxiety in patients with life-threatening cancer: a randomized double-blind trial*, Journal of Psychopharmacology 30(12), 1181-1197 (2016)).

N,N-dimethyltryptamine (hereinafter "DMT") is also understood to hold therapeutic value as a psychedelic, with efficacy trials ongoing to assess the effect of DMT or DMT fumarate administered intravenously to subjects with major depressive disorder ("MDD"). However, although the intrinsic properties of DMT make it an attractive possible medication, especially for neurological diseases and conditions, current therapeutic compositions and modes of administration complicate treatment and may not provide optimal therapeutic results. For example, when smoked or delivered intravenously, DMT has a very fast onset of action and a short duration of effect, which presents a challenge to determine a suitable administration regimen with appropriate dosage and frequency of administration of DMT to provide effective therapy for neurological diseases and conditions. This is especially true for neurological diseases and conditions which would benefit from the presence of therapeutic blood levels of DMT over a more extended period of time following administration than can be achieved with a single dose of DMT via injection or inhalation.

Therefore, a significant need exists for readily administrable medications of DMT to treat neurological diseases and conditions. Such medications, which maximize efficacy while enabling drug side effects to be effectively controlled, are of particular interest, especially if administrable via a convenient route, including self-administration. The present disclosure solves this need by providing novel compositions comprising DMT or a pharmaceutically acceptable salt thereof which, when administered intranasally, buccally, sub-lingually or by subcutaneous injection, have a rapid onset of action, but also extend the effective duration of action of DMT when compared to DMT administered by IV injection or inhalation.

SUMMARY OF THE INVENTION

In one aspect, the present disclosure provides a pharmaceutical composition comprising DMT or a pharmaceutically acceptable salt thereof, wherein following administration to a subject, the DMT human blood plasma Tmax is between from about 1 minute to about 60 minutes, or about 1.5 minutes to about 45 minutes, or about 1.7 minutes to about 35 minutes, or about 2 minutes to about 30 minutes, or about 2 minutes to about 20 minutes (e.g. about 5 minutes to about 15 minutes, especially about 5, 6, 7, 8, 9 or 10 minutes). Preferably, after Tmax is achieved, the concentration of DMT is maintained at about 50% or more, preferably 80% or more, of Cmax for between about 10 minutes to about 30 minutes (e.g. about 10, about 15, about 20, about 25, about 30 minutes).

In one embodiment, the pharmaceutical composition comprising DMT or a pharmaceutically acceptable salt thereof is administered buccally, sublingually, subcutaneously or intranasally.

In one aspect, the present disclosure provides a pharmaceutical composition comprising DMT or a pharmaceutically acceptable salt thereof, wherein following buccal, sublingual, subcutaneous or intranasal administration to a subject, blood levels of DMT are maintained at a therapeutically effective blood level, preferably at a concentration at or above about 250 nmol/L (or 47.07 ng/mL free base equivalent at 188.27 g/mol) for at least about 10 minutes (e.g. about 10, about 15, about 20, about 25, about 30, about 35, about 40, about 45 or about 50 minutes) and preferably then reduced to about 10% or less of Cmax within about 20 minutes or less (e.g. about 10, about 15 or about 20 minutes)

In one aspect, the present disclosure provides a pharmaceutical composition comprising DMT or a pharmaceutically acceptable salt thereof, wherein following buccal, sublingual, subcutaneous or intranasal administration to a subject, the human blood plasma T % is about 5 minutes to about 20 minutes, e.g. about 10 minutes to about 20 minutes.

In one aspect, the present disclosure provides a pharmaceutical composition comprising DMT or a pharmaceutically acceptable salt thereof, wherein following buccal, sublingual, subcutaneous or intranasal administration to a subject at a dose of about 5 mg to about 80 mg (e.g. about 50 mg), about 100% of the drug is released from the composition within about 15 minutes to about 50 minutes, e.g. about 20 minutes to about 30 minutes.

In one embodiment of any of the previous aspects, the drug is delivered transmucosally.

In one embodiment of any of the previous aspects, the pharmaceutical composition is administered intranasally. In a particular embodiment, the drug is absorbed across the nasal mucosa.

In one embodiment of any of the previous aspects, the pharmaceutical composition is administered buccally. In a particular embodiment, the drug is absorbed across the buccal mucosa.

In one embodiment of any of the previous aspects, the pharmaceutical composition is administered sublingually. In a particular embodiment, the drug is absorbed across the sublingual mucosa.

In one embodiment of any of the previous aspects, the pharmaceutical composition is administered subcutaneously. In a particular embodiment, the pharmaceutical composition is administered by subcutaneous injection.

In one aspect, the present disclosure provides a method of treating a neurological disease or condition, comprising administering transmucosally to a subject an effective amount of DMT or a pharmaceutically acceptable salt thereof. In one embodiment of this aspect, the drug is absorbed across the buccal mucosa. In one embodiment of this aspect, the drug is absorbed across the sublingual mucosa. In one embodiment of this aspect, the drug is absorbed across the nasal mucosa.

In one aspect, the present disclosure provides a method of treating a neurological disease or condition, comprising administering subcutaneously to a subject an effective amount of DMT or a pharmaceutically acceptable salt thereof. In one embodiment of this aspect, the drug is administered by subcutaneous injection.

BRIEF DESCRIPTION OF THE DRAWINGS

Various objects and advantages, and a more complete understanding, of the present disclosure are apparent and more readily appreciated by reference to the following Detailed Description and Claims when taken in conjunction with the accompanying Drawings wherein:

DETAILED DESCRIPTION

Drugs can be absorbed through mucosal surfaces, such as those in the nasal passage and in the oral cavity. Drug delivery via mucosal surfaces can be efficient because they lack the stratum corneum of the epidermis, a major barrier to absorption across the skin. Mucosal surfaces are also typically rich in blood supply, which can rapidly transport drugs systemically while avoiding significant degradation by first-pass hepatic metabolism.

There are three routes of absorption for drugs sprayed onto the olfactory mucosa, including by the olfactory neurons, by the supporting cells and surrounding capillary bed, and into the cerebro-spinal fluid. Absorption by olfactory neurons and into the cerebrospinal fluid has the potential for direct effects on the brain, whilst minimizing systemic concentrations. Absorption of drugs through the nasal mucosa tends to be rapid.

Like intranasal administration, oral transmucosal absorption is generally rapid because of the rich vascular supply to the mucosa and the lack of a stratum corneum in the epidermis. Such drug transport typically provides a rapid rise in blood concentrations, and similarly avoids the enterohepatic circulation and immediate destruction by gastric acid or partial first-pass effects of gut wall and hepatic metabolism.

The present disclosure is based, in one aspect, on the discovery of certain compositions of DMT or a pharmaceutically acceptable salt thereof which provide rapid onset of the drug following administration to the subject in need thereof, especially when the drug is administered transmucosally by the nasal, buccal or sublingual route, but also when given subcutaneously. The rapid onset is, in a particular aspect of the present disclosure, followed by a period of effective DMT exposure which can exceed the effective exposure period achievable when the same drug is administered intravenously.

Compositions of the present disclosure, in another aspect, can achieve a prolonged period of exposure of DMT at therapeutically effective levels followed by a rapid offset. Thus, for example, therapeutically effective blood levels of DMT may be maintained for up to from about 15 minutes to about 60 minutes following administration after which time there is a rapid decline in DMT blood levels. For example, over a period of about 20 minutes or less, the decline in DMT blood levels may result in blood containing DMT at a level of about 10% Cmax or less. In one aspect, 100% of DMT is released within about 60 minutes following administration.

The unique PK profile exhibited by compositions of the present disclosure leads to particular benefits when treating neurological diseases or conditions. Such compositions are superior to compositions of DMT or a pharmaceutically acceptable salt thereof which exhibit (1) a harsh onset effect (e.g. caused by very rapid onset) (2) a shorter period of therapeutic exposure of DMT and/or (3) a slower offset.

Thus, the present disclosure relates to new pharmaceutical compositions comprising DMT or a pharmaceutically acceptable salt thereof, together with uses thereof, particularly for the treatment of a neurological disease or condition. Specifically, the disclosure provides, in one aspect, pharmaceutical compositions comprising DMT or a pharmaceutically acceptable salt thereof which exhibit, following transmucosal (e.g. buccal, sublingual or intranasal) administration to a subject, rapid onset, an extended period of therapeutic exposure of DMT and rapid offset. The disclosure also provides, in a second aspect, pharmaceutical compositions comprising DMT or a pharmaceutically acceptable salt thereof which exhibit, following subcutaneous administration to a subject, rapid onset, an extended period of therapeutic exposure of DMT and rapid offset.

Definitions

As used herein, the following terms are defined with the following meanings, unless explicitly stated otherwise:

The term "about" when used before a numerical designation, e.g., pH, temperature, amount, or concentration, indicates an approximation which may vary by up to (+) or (−) 5%.

The singular form "a", "an" and "the" include plural references unless the context clearly dictates otherwise. For example, the term "a pharmaceutically acceptable carrier" may include a plurality of pharmaceutically acceptable carriers, including mixtures thereof.

The term "and/or" is intended to mean either or both of two components of the invention.

The term "subject," "individual" and "patient" are used interchangeably herein, and refers to a human.

The term "device," as used herein, refers to an apparatus or system capable of delivering a drug to a patient in need thereof.

The term "in need of treatment" and the term "in need thereof" when referring to treatment are used interchangeably and refer to a judgment made by a caregiver (e.g. physician, nurse, nurse practitioner) that a patient will benefit from treatment.

The terms "treat" and "treatment" refer herein to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition. "Treatment" can also mean prolonging survival as compared to expected survival if not receiving treatment. Those in need of treatment include those already with the disease or condition as well as those prone to having the disease or condition or those in which the disease or condition is to be prevented. "Treatment" can, when concerning depression, also include reducing at least one sign or symptom of depression. Examples of a sign or symptom of depression include depressed mood, diminished interest in activities, weight loss or gain, decrease or increase in appetite, insomnia or hypersomnia, psychomotor agitation or retardation, fatigue or loss of energy, feelings of worthlessness or excessive or inappropriate guilt, diminished ability to concentrate or indecisiveness, or suicidal ideation or behavior.

The term "nasal delivery", "intranasal delivery", "nasal administration" or "intranasal administration" refers to a route of administration wherein the pharmaceutical dosage form is taken to, or through, the nose (e.g., nasal cavity). Similarly, a "nasal delivery device" or an "intranasal delivery device" is intended to mean an apparatus that administers a drug into the nasal cavity. Non-limiting examples of intranasal administration include introduction of a solution or suspension in the form of a nasal spray or drops (direct instillation) or intranasal application of a gel, emulsion or ointment.

The term "buccal delivery" or "buccal administration" refers to a route of administration in which the pharmaceutical dosage form is applied between the patient's cheek and gum (i.e. the buccal cavity).

The term "sublingual delivery" refers to a route of administration in which the pharmaceutical dosage form is applied under the patient's tongue.

The term "subcutaneous delivery" refers to a route of administration in which the pharmaceutical dosage form is injected with a short needle into the tissue layer between the skin and the muscle.

The term "pharmaceutically acceptable" as used herein, refers to a component of a pharmaceutical composition that is compatible with the other ingredients of the formulation and not overly deleterious to the recipient thereof.

The term "pharmaceutically acceptable salt" as used herein with reference to "DMT or a pharmaceutically acceptable salt thereof" means a pharmaceutically acceptable acid addition salt. Typically, acidic reagents may be used to prepare salts, in particular pharmaceutically acceptable salts, of DMT. Examples of suitable acidic reagents include fumaric acid, hydrochloric acid, tartaric acid, citric acid, hydrobromic acid, sulfuric acid, phosphoric acid, acetic acid, maleic acid, lactic acid, tartaric acid and gluconic acid. Often, the form of the DMT salt in a pharmaceutical composition of the present disclosure or otherwise used according to the various aspects of the present disclosure, and embodiments thereof, is a pharmaceutically acceptable salt of a fumarate, hydrochloride, tartrate or citrate salt, e.g. a fumarate salt.

The term "carrier" refers to a diluent, adjuvant, excipient, or vehicle with which the therapeutic is administered and includes, but is not limited to, such liquids and powders that are hydrophilic substances, hydrophobic substances and substances that possess both hydrophilic and hydrophobic properties such as emulsifiers.

The term "effective amount" or "therapeutically effective amount" as used herein, refers to the amount of active agent that elicits the biological or medicinal response in a tissue, system, or individual that is being sought by a researcher, healthcare provider or individual.

The term "neurological disease or condition" as used herein, means a disease or condition selected from: a neuropsychiatric disorder, such as depression (including severe depression such as treatment-resistant depression, major depressive disorder and persistent depressive disorder), catatonic depression, a depressive disorder due to a medical condition, postpartum depression, premenstrual dysphoric disorder, or seasonal affective disorder, anxiety, anxiety disorder, social anxiety disorder, general anxiety disorder (GAD), avolition disorder, bipolar disorder (including bipolar I disorder and bipolar II disorder), post-traumatic stress disorder, body dysmorphic disorder, abnormalities of mood or emotion, including the above conditions, dysthymia, schizoaffective disorder, schizophrenia and other psychotic disorders, panic disorder, traumatic stress disorders, phobic disorders, and personality disorders with abnormal mood, such as borderline personality disorder, schizoid and schizotypal disorders and suicide ideation, or rumination/unproductive repetitive thoughts negatively impacting one's behavior/mood/ability to focus, obsessive-compulsive disorder, addiction (including substance use disorder such as addiction to nicotine, alcohol, cocaine, opioids, amphetamine, methamphetamine, heroin, morphine, phencyclidine, 3,4-methylenedioxy-methamphetamine, as well as other addictive substances), addictive behavior (including eating, gambling, sex, pornography, videogames, work, exercise, spiritual obsession, self-harm, travel and shopping addiction), eating disorder (including anorexia nervosa, bulimia nervosa and binge eating disorder), and pain (including pain associated with migraine or headache or chronic pain).

As used herein, the term "treatment-resistant depression" or "TRD" means a depressive disorder which does not respond satisfactorily to adequate treatment. TRD is a complex phenomenon influenced by variety in depressive subtypes, psychiatric comorbidity, and coexisting medical illnesses. Although TRD episodes are most commonly associated with major depressive disorder (MDD), they are also seen in the depressed phase of bipolar disorder.

As used herein, the term "onset" means the time to achieve maximum blood plasma concentration following administration (i.e. Tmax) and may also be described as "onset of action". A "rapid onset" in the context of the present disclosure means that the drug achieves Cmax within about 20 minutes (e.g. within about 2-10 minutes). However, onset following administration of a composition according to the present disclosure is less rapid, and consequently less "harsh" to the patient, than if DMT is administered by IV injection.

As used herein, the term "offset" means the time between the last time the concentration of DMT is at Cmax±10% and the first time the plasma concentration of DMT reduces to a threshold level below which the drug no longer has any meaningful therapeutic effect (e.g. about 250 nmol/L or 47.07 ng/mL). A "rapid offset" in the context of the present disclosure means less than about 10 minutes. However, although rapid, the offset is still sufficiently long for the drug to exert a reasonable duration of psychedelic effects.

Pharmaceutical Compositions and Delivery

Pharmaceutical compositions comprising DMT or a pharmaceutically acceptable salt thereof suitable for intranasal administration include compositions wherein the active ingredient is present in a liquid carrier. In various embodiments, the composition may be in the form of an aqueous or non-aqueous solution, suspension, liposomal dispersion, emulsion, microemulsion or sol-gel. The carrier can contain additives such as solubilizing agents, e.g., propylene glycol, surfactants, absorption enhancers such as lecithin (phosphatidylcholine) or cyclodextrin, mucoadhesives and/or preservatives such as parabens. Methods well known in the art for making intranasal formulations may be found, for example, in Remington, 2000. Further, methods for formulating compounds for intranasal administration, including extending the presence of the active agent in the nasal cavity, combining with agents to enhance solubility, and increasing bioavailability, etc. are well known.

Pharmaceutical compositions comprising DMT or a pharmaceutically acceptable salt thereof suitable for buccal and sublingual administration include rapidly dissolving tablets, wafers, films, strips or patches, orodispersible tablets, oral gels, medicated lollipops, sprays, drops, and other formulations that are retained on the buccal or sublingual mucosal surface.

Pharmaceutical compositions comprising DMT or a pharmaceutically acceptable salt thereof suitable for subcutaneous administration may be provided in unit dosage forms (e.g., in single-dose ampoules), or in vials containing several doses and in which a suitable preservative may be added (see below). The composition may conveniently be in the form of a solution, a suspension or an emulsion, or it may be presented as a dry powder to be reconstituted with water or another suitable vehicle before use. Apart from DMT or a pharmaceutically acceptable salt thereof, the composition may include suitable parenterally acceptable carriers and/or excipients. Furthermore, the composition may include suspending, solubilizing, stabilizing, pH-adjusting agents, and/or dispersing agents.

Pharmaceutical compositions of the present disclosure may include one or more excipients, diluents, binders, lubricants, glidants, disintegrants, desensitizing agents, emulsifiers, mucosal adhesives, solubilizers, suspension agents, viscosity modifiers, ionic tonicity agents, buffers, carriers, surfactants, or mixtures thereof. Pharmaceutical compositions of the present disclosure may also include components such as permeation enhancers, bioadhesive polymers, and means for providing modified release, such as sustained release, of the active ingredient. The compositions can also include one or more pharmaceutically acceptable flavoring or other taste-masking agent.

The rates of in vivo release and in vivo clearance of DMT may be influenced by means well known in the art. For example, incorporation of the active material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Also comprehended herein are compounds modified by the covalent attachment of water-soluble polymers such as polyethylene glycol, copolymers of polyethylene glycol and polypropylene glycol, carboxymethyl cellulose, dextran, polyvinyl alcohol, cyclodextrin, cucurbituril, polyvinylpyrrolidone or polyproline. The modified compounds may exhibit substantially longer half-lives in blood following administration than do the corresponding unmodified compounds.

Depending on the delivery device employed, delivery between about 25% and about 100% of the drug product, i.e., DMT is achieved. It is to be understood however, that due to the nature of drug delivery devices, one of ordinary skill in the art will appreciate that not all of the drug can be delivered as it is the function of the delivery device employed. Thus, for clarity, it is to be understood that about 25% to about 100% of the drug product delivered is dependent on the selected drug delivery method and/or device. Therefore, 100% of the drug product delivered may not be all of the drug product, but it will be all of the drug product a selected device is capable of delivering.

Intranasal Compositions

Relative to an oral dosage form such as a tablet or capsule, intranasal delivery provides for rapid absorption, faster onset of therapeutic action and avoidance of gut wall or liver first pass metabolism. For patients who have difficulty in swallowing tablets, capsules or other solids or those who have intestinal failure, the intranasal delivery route may be preferred.

The compositions of the present disclosure for nasal administration include DMT or a pharmaceutically acceptable salt thereof, and optionally can also comprise other ingredients including, but not limited to, carriers and excipients, such as absorption-promoting agents which promote nasal absorption of the active ingredient after nasal administration and agents to improve brain penetration of the drug following nasal administration. Other optional excipients include diluents, binders, lubricants, glidants, disintegrants, desensitizing agents, emulsifiers, mucosal adhesives, solubilizers, suspension agents, viscosity modifiers, ionic tonicity agents, buffers, carriers, flavors and mixtures thereof. In one embodiment, the particle size of the active ingredient is less than or equal to about 60 microns, which can help to ensure uniformity of any blends of the particles with other ingredients, or to provide an adequate dispersion in a liquid vehicle.

The amount of drug absorbed depends on many factors. These factors include the drug concentration, the drug delivery vehicle, mucosal contact time, the venous drainage of the mucosal tissues, the degree that the drug is ionized at the pH of the absorption site, the size of the drug molecule, and its relative lipid solubility. Those of skill in the art can readily prepare an appropriate intranasal composition, which delivers an appropriate amount of the active agent, taking these factors into consideration.

The transport of the active ingredient across normal mucosal surfaces (such as the nasal or buccal mucosa) can be enhanced by optionally combining it with an absorption promoting agent. Examples of these absorption promoting agents include, but are not limited to, cationic polymers, surface active agents, chelating agents, mucolytic agents, cyclodextrin, polymeric hydrogels, combinations thereof, and any other similar absorption promoting agents known to those of skill in the art. Representative absorption promoting excipients include phospholipids, such as phosphatidylglycerol or phosphatidylcholine, lysophosphatidyl derivatives, such as lysophosphatidylethanolamine, lysophosphatidylcholine, lysophosphatidylglycerol, lysophosphatidylserine, or lysophosphatidic acid, polyols, such as glycerol or propylene glycol, fatty acid esters thereof such as glycerides, amino acids, and esters thereof, and cyclodextrins. Gelling excipients or viscosity-increasing excipients can also be used.

The transport of the active ingredient across normal mucosal surfaces can also be enhanced by increasing the time in which the formulations adhere to the mucosal surfaces. Mucoadhesive/bioadhesive polymers, for example, those which form hydrogels, exhibit muco-adhesion and controlled drug release properties and can be included in the intranasal or buccal, compositions described herein. Representative bioadhesive or hydrogel-forming polymers capable of binding to the nasal mucosa are well known to those of skill in the art, and include polycarbophil, polylysine, methylcellulose, sodium carboxymethylcellulose, hydroxypropyl-methylcellulose, hydroxyethyl cellulose, pectin, Carbopol 934P, polyethylene oxide 600K, one or more poloxomers such as Pluronic F127 and/or Pluronic F-68, polyisobutylene (PIB), polyisoprene (PIP), polyvinyl pyrrolidone (PVP), polyvinyl alcohol (PVA), xanthum gum, guar gum, and locust bean gum. Other nasal delivery compositions are chitosan-based and are suitable to increase the residence time of the active ingredient on mucosal surfaces, which results in increasing its bioavailability. Thiolated polymeric excipients that form covalent bonds with the cysteine-rich subdomains of the mucus membrane can also provide mucoadhesion, which prolongs the contact time between the active ingredient and the membrane.

The intranasal compositions can also include one or more preservatives. Representative preservatives include quaternary ammonium salts such as lauralkonium chloride, benzalkonium chloride, benzododecinium chloride, cetyl pyridium chloride, cetrimide, domiphen bromide; alcohols such as benzyl alcohol, chlorobutanol, o-cresol, phenyl ethyl alcohol; organic acids or salts thereof such as benzoic acid, sodium benzoate, potassium sorbate, parabens; or complex forming agents such as EDTA.

The carriers and excipients include ion-exchange microspheres which carry suitable anionic groups such as carboxylic acid residues, carboxymethyl groups, sulphopropyl groups and methylsulphonate groups. Ion-exchange resins, such ascation exchangers, can also be used. Chitosan, which is partially deacetylated chitin, or poly-N-acetyl-D-glucosamine, or a pharmaceutically acceptable salt thereof such as hydrochloride, lactate, glutamate, maleate, acetate, formate, propionate, malate, malonate, adipate, or succinate. Suitable other ingredients for use as non-ion-exchange microspheres include starch, gelatin, collagen and albumin.

The composition can also include an appropriate acid selected from the group consisting of hydrochloric acid, lactic acid, glutamic acid, maleic acid, acetic acid, formic acid, propionic acid, malic acid, malonic acid, adipic acid, and succinic acid. Other ingredients such as diluents are cellulose, microcrystalline cellulose, hydroxypropyl cellulose, starch, hydroxypropylmethyl cellulose, and the like. Excipients to adjust the tonicity of the composition may be added such as sodium chloride, glucose, dextrose, mannitol, sorbitol, lactose, and the like. Acidic or basic buffers can also be added to the intranasal composition to control the pH.

In addition to using absorption enhancing agents, which increase the transport of the active agents through the mucosa, and bioadhesive materials, which prolong the contact time of the active agent along the mucosa, the administration of the active agent can be controlled by using controlled release formulations. There are numerous particulate drug delivery vehicles known to those of skill in the art which can include the active ingredients and deliver them in a controlled manner. Examples include particulate polymeric drug delivery vehicles, for example, biodegradable polymers, and particles formed of non-polymeric components. These particulate drug delivery vehicles can be in the form of powders, microparticles, nanoparticles, microcapsules, liposomes, and the like. Typically, if the active agent is in particulate form without added components, its release rate depends on the release of the active agent itself. Typically, the rate of absorption is enhanced by presenting the drug in a micronized form, wherein particles are below 20 microns in diameter. In contrast, if the active agent is in particulate form as a blend of the active agent and a polymer, the release of the active agent is controlled, at least in part, by the removal of the polymer, typically by dissolution, biodegradation, or diffusion from the polymer matrix.

Intranasal Delivery

Intranasal delivery devices are known in the art. Thus, any device suitable for delivery of drug to nasal mucosa may be used. Non-limiting examples of devices useful for the administration of liquid compositions include vapor devices (e.g., vapor inhalers), drop devices (e.g., catheters, single-dose droppers, multi-dose droppers, and unit-dose pipettes), mechanical spray pump devices (e.g., squeeze bottles, multi-dose metered-dose spray pumps, and single/duo-dose spray pumps), bi-directional spray pumps (e.g., breath-actuated nasal delivery devices), gas-driven spray systems/atomizers (e.g., single- or multi-dose HFA or nitrogen propellant-driven metered-dose inhalers, including traditional and circumferential velocity inhalers), and electrically powered nebulizers/atomizers (e.g., pulsation membrane nebulizers, vibrating mechanical nebulizers, and hand-held mechanical nebulizers). Non-limiting examples of devices useful for the administration of powder compositions (e.g., lyophilized or otherwise dried pooled compositions) include mechanical powder sprayers (e.g., hand-actuated capsule-based powder spray devices and hand-actuated powder spray devices, hand actuated gel delivery devices), breath-actuated inhalers (e.g., single- or multi-dose nasal inhalers and capsule-based single- or multi-dose nasal inhalers), and insufflators (e.g., breath-actuated nasal delivery devices).

Use of metered sprays for intranasal delivery can also be accomplished by including the active ingredient in a solution or dispersion in a suitable medium which can be administered as a spray. Representative devices of this type are disclosed in the following patents, patent applications, and publications: WO03/026559, WO02/011800, WO00/51672, WO02/068029, WO02/068030, WO02/068031, WO02/068032, WO03/000310, WO03/020350, WO03/082393, WO03/084591, WO03/090812, WO 00/41755, and the pharmaceutical literature (See, Bell, A. Intranasal Delivery Devices, in Drug Delivery Devices Fundamentals and Applications, Tyle P. (ed), Dekker, New York, 1988), Remington's Pharmaceutical Sciences, Mack Publishing Co., 1975, all of which are incorporated herein by reference.

In addition to the foregoing, the compounds can also be administered intranasally in the form of irrigations and douches, as is known in the art. Nasal irrigation involves regularly flooding the nasal cavity with solution, which includes the drug. Nasal douches are typically used by filling a nasal douche with a solution including the drug, inserting the nozzle from the douche into one nostril, opening one's mouth to breathe, and causing the solution to flow into one nostril, rinse round the septum, and discharge from the other nostril.

Means to deliver drug to the upper portion of the nasal cavity, such as the cribriform, are of particular interest herein. Also of interest is delivery of drug along the trigeminal nerve pathway.

Buccal and Sublingual Compositions and Delivery

Relative to an oral dosage form such as a tablet or capsule, oral transmucosal delivery can, like intranasal delivery, provide for rapid absorption, faster onset of therapeutic action and avoidance of liver or gut wall first pass metabolism. For patients who have difficulty in swallowing tablets, capsules or other solids or those who have intestinal failure, the buccal or sublingual delivery route is preferred.

Compositions for buccal or sublingual administration include DMT or a pharmaceutically acceptable salt thereof and at least one excipient to form a solid dosage form. The solid dosage form disintegrates in an oral cavity or under the tongue with minimal liquid exposure and at body temperature, and ideally adheres to the body tissue of the oral cavity or the tissue under the tongue via direct adhesion to tissue or, in the case of buccal administration, entrapment of the dosage form in-between the gum and inner cheek. The solid dosage form disintegrates or melts at body temperature with or without the aid of fluids, salivary fluids, mechanical erosion, or combinations thereof. Alternatively, the dosage form can be sprayed into the oral cavity or under the tongue in the form of a solution spray or a dry powder. Generally, the composition can be adhesive towards the body tissue lining the patient's oral cavity or under the tongue.

The dosage form can be, but is not limited to, tablets, a bioadhesive patch or film, sponges, lozenges, hard candies, wafers, lollipops, sprays, gums, pills, pellets, spheres, combinations thereof, and other forms known to those of skill in the art.

A buccal or sublingual film represents a particularly convenient vehicle for administering a pharmaceutical composition of the present disclosure. Examples of films include, in one aspect, a composition comprising DMT or a pharmaceutically acceptable salt thereof in a mucoadhesive polymer. Suitable mucoadhesive polymers include one or more polymers selected from cellulose derivatives, polyacrylic acids, polyacrylates, polyethylene oxides, polyvinyl pyrrolidones, polyvinyl alcohols, tragacanth, alginates, gum (including karaya gum, guar gum, xanthan gum), soluble starch, gelatin, lectin, pectin, and chitosan. In some embodiments, the mucoadhesive polymer comprises one or more polymers selected from a hydrophilic polymer, a polysaccharide and its derivatives, and a hydrogel. In some embodiments, the mucoadhesive polymer comprises one or more polymers selected from polyacrylic acids, polyacrylates, celluloses, e.g., carboxycelluloses (e.g., sodium carboxymethyl cellulose), hydroxyalkyl cellulose (e.g, hydroxypropylcellulose, hydroxyethylcellulose and hydroxyethyl ethyl cellulose), polyvinylpyrrolidone, and polyvinyl alcohol. In some embodiments, the mucoadhesive polymer comprises one or more polymers selected from Carbopol (polyacrylic acid), carboxymethyl cellulose, carboxyethyl cellulose, hydroxypropyl cellulose, hydroxypropylmethyl cellulose, and gum. In some embodiments, the mucoadhesive polymer is water-swellable. Typically, the mucoadhesive polymer is present in an amount of about 15% to about 60% by weight of the film composition.

The film compositions can further include a permeation enhancer and/or an antioxidant. For example, in some embodiments, the film composition comprises a permeation enhancer, e.g., comprising one or more permeation enhancers selected from dimethyl sulfoxide (DMSO), oleic alcohol, oleic acid, oleyl oleate, levulinic acid, propylene glycol, dipropylene glycol, ethanol, and surfactants. In some embodiments, the permeation enhancer is present in an amount of about 5% to about 30% by weight of the film composition. In some embodiments, the film composition comprises an antioxidant, e.g., tocopherol acetate, α-tocopherol, L-glutathione, L cysteine, ascorbic acid, ascorbyl palmitate, propyl gallate, butylated hydroxytoluene (BHT), butylated hydroxy anisole (BHA), tocobiol and ethylenediaminetetraacetic acid (EDTA).

In some embodiments, the film compositions can form a bilayer or multilayer film composition. Typically, such a bilayer or multilayer film can provide a bi-phasic release profile, which can be advantageous in certain situations. In some embodiments, a quick-release film layer comprises a water-soluble polymer. In some embodiments, the water-soluble polymer in the quick-release film comprises one or more polymers selected from hydroxypropyl methyl cellulose (HPMC), hydroxylpropyl cellulose (HPC), povidone, copovidone, polyvinyl alcohols (PVA), low molecular weight polyethylene oxide, and starch-based polymers. In some embodiments, the quick-release film can also optionally include a permeation enhancer, e.g., one or more permeation enhancers selected from dimethyl sulfoxide (DMSO), oleic alcohol, oleic acid, oleyl oleate, levulinic acid, propylene glycol, dipropylene glycol, ethanol, and surfactants. In some embodiments, the quick-release film can also optionally include an antioxidant, such as tocopherol acetate.

There are numerous compositions and delivery vehicles suitable for buccal or sublingual delivery of the active ingredients. In addition to DMT or a pharmaceutically acceptable salt thereof, other components of dosage forms include, but are not limited to, starch, mannitol, xylitol, saccharin, sucralose, I-menthol, citric acid, I-glutathione, kaolin, calcium sulfate, inorganic salts, such as sodium chloride, powdered cellulose derivatives, dibasic and tribasic calcium phosphate, calcium sulfate, magnesium carbonate, magnesium oxide, poloxamers such as polyethylene oxide, hydroxypropyl methylcellulose, anionic excipients, cationic excipients, zwitterionic excipients, with reference to U.S. Pat. No. 6,436,950, which is incorporated herein by reference with regard to such excipients, polymeric hydrogel, powder microsphere mucoadhesive compositions, thiolated polymeric excipients, polycationic material, chitosan, cross-linked starches, fats, carbohydrates, polyols, buffers, phosphate buffers, acetate buffers, methocel, sodium chloride, water, lactic acid, benzalkonium chloride, demineralized water, cellulose, microcrystalline cellulose, hydroxypropyl cellulose, hydrogenated vegetable oil, flavoring agents, phospholipids, xylitol, cacao, combinations thereof, and other similar excipients known to those of skill in the art. Plasticizers can also be present. Representative plasticizers include, polyethylene glycols, propylene glycols, castor oil, vegetable oil etc.

Binders can also be present. Suitable binders include substances such as celluloses, including but not limited to cellulose, methylcellulose, ethylcellulose, hydroxypropyl cellulose and hydroxymethylcellulose, polypropylpyrrolidone, polyvinylpyrrolidone, gelatin, polyethylene glycol, starch, natural gums such as acacia, alginates, guar, and gum arabic) and synthetic gums and waxes.

Subcutaneous Compositions and Delivery

For subcutaneous administration, aqueous suspensions, isotonic saline solutions and sterile injectable solutions may be used, optionally containing pharmaceutically acceptable excipients, which may include dispersing agents and/or wetting agents, such as propylene glycol or butylene glycol.

In addition, suspensions of DMT or a pharmaceutically acceptable salt thereof may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, DMT or a pharmaceutically acceptable salt thereof may be in powder form for constitution with a suitable vehicle, e.g., sterile pyrogen-free water, before use. The solution or suspension may be administered subcutaneously to the subject by injection using well-known devices and techniques. Any appropriate syringe may conveniently be used, including an autoinjector which may allow self-administration.

Dosing

The dosage amount of DMT or a pharmaceutically acceptable salt thereof administered to a patient, as defined herein, with a neurological disease or condition, is typically from about 0.1 mg/kg to about 1 mg/kg. A typical human dose (for an adult weighing 50-80 kg) would equate to a dose of about 5 mg to about 80 mg. In one embodiment, the dose is about 10 mg to about 60 mg, such as about 20-60 mg, about 30-60 mg, about 40-60 mg, or any specific amount therebetween, including 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, and 60 mg. In this disclosure, when ranges are set forth, such as "about 20-60 mg" the inventor contemplates all discrete values within that range, some of which are specifically mentioned, but all of which are not, simply for the purpose of brevity.

In a particular embodiment, DMT or a pharmaceutically acceptable salt thereof may be administered to a patient in one or more doses over a 24 hour period, e.g. 1, 2, 3, 4 or 5 doses. However, the total dose administered to the subject should not exceed about 100 mg over a 24 hour period.

Uses

In one aspect, the present disclosure provides a pharmaceutical composition, as further described herein, for use in treating a neurological disease or condition.

In one aspect, the present disclosure provides a method of treating a neurological disease or condition, comprising administering transmucosally to a subject an effective amount of DMT or a pharmaceutically acceptable salt thereof.

In one aspect, the present disclosure provides a method of treating a neurological disease or condition, comprising administering intranasally to a subject an effective amount of DMT or a pharmaceutically acceptable salt thereof.

In one aspect, the present disclosure provides a method of treating a neurological disease or condition, comprising administering buccally to a subject an effective amount of DMT or a pharmaceutically acceptable salt thereof.

In one aspect, the present disclosure provides a method of treating a neurological disease or condition, comprising administering sublingually to a subject an effective amount of DMT or a pharmaceutically acceptable salt thereof.

In one aspect, the present disclosure provides a method of treating a neurological disease or condition, comprising administering subcutaneously to a subject an effective amount of DMT or a pharmaceutically acceptable salt thereof.

In any one of the abovementioned aspects the neurological disease or condition may be, for example, a neuropsychiatric disorder.

Examples of neuropsychiatric disorders which may be treated with DMT or a pharmaceutically acceptable salt thereof include depression (e.g. TRD), anxiety, bipolar disorder, post-traumatic stress disorder, abnormalities of mood or emotion, including the above conditions, dysthymia, schizoaffective disorder, schizophrenia and other psychotic disorders, panic disorder, traumatic stress disorders, phobic disorders, eating disorders and personality disorders with abnormal mood, such as borderline personality disorder, schizoid and schizotypal disorders and suicide ideation, or rumination/unproductive repetitive thoughts negatively impacting one's behavior/mood/ability to focus.

In any one of the abovementioned aspects the neurological disease or condition may be, for example, addiction.

Examples of addiction which may be treated with DMT or a pharmaceutically acceptable salt thereof include substance use disorder such as addiction to nicotine, alcohol, cocaine, opioids, amphetamine, methamphetamine, heroin, morphine, phencyclidine, 3,4-methylenedioxy-methamphetamine, as well as other addictive substances.

In any one of the abovementioned aspects the neurological disease or condition may be, for example, addictive behavior.

Examples of addictive behavior which may be treated with DMT or a pharmaceutically acceptable salt thereof include addiction to eating, gambling, sex, pornography, videogames, work, exercise, spiritual obsession, self-harm, travel, shopping and substance use disorder (SUD).

In a particular embodiment, the present disclosure provides a method of treating depression (including severe depression such as treatment-resistant depression, major depressive disorder and persistent depressive disorder, catatonic depression, a depressive disorder due to a medical condition, or postpartum depression), comprising administering transmucosally (e.g. buccally, sublingually or intranasally) to a subject an effective amount of DMT or a pharmaceutically acceptable salt thereof.

In a particular embodiment, the present disclosure provides a method of treating depression (including severe depression such as treatment-resistant depression, major depressive disorder and persistent depressive disorder, catatonic depression, a depressive disorder due to a medical condition, or postpartum depression), comprising administering subcutaneously to a subject an effective amount of DMT or a pharmaceutically acceptable salt thereof.

Combination Therapy

The methods described herein include administering DMT or a pharmaceutically acceptable salt thereof as the sole active ingredient. However, also encompassed within the scope of the present disclosure are methods for treating a neurological disease or condition that comprise administering DMT or a pharmaceutically acceptable salt thereof in combination with one or more additional agents.

In one aspect, these additional agents are therapeutic agents appropriate for the disease or disorder that is being treated, as is known in the art. In some embodiments, DMT or a pharmaceutically acceptable salt thereof may be administered to the subject in combination with one or more anti-depressant or anti-anxiety drugs, such as SSRIs, tricyclic antidepressants (TCAs), monoamine oxidase inhibitors (MAOIs), or serotonin norepinephrine reuptake inhibitors (SNRIs).

In some embodiments, the disclosure provides a method of reducing anxiety in a subject undergoing treatment with DMT or a pharmaceutically acceptable salt thereof, the method comprising administering to the subject: i) DMT or a pharmaceutically acceptable salt thereof and ii) one or more benzodiazepines.

In some embodiments, the one or more benzodiazepines are administered to the subject at or around the same time as DMT or a pharmaceutically acceptable salt thereof. In some embodiments, the one or more benzodiazepines are administered to the subject prior to administration of DMT or a pharmaceutically acceptable salt thereof, such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof. In some embodiments, the one or more benzodiazepines are administered to the subject after DMT or a pharmaceutically acceptable salt thereof, such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

In some embodiments, the benzodiazepine is selected from the group consisting of adinazolam, alprazolam, bentazepam, bretazenil, bromazepam, bromazolam, brotizolam, camazepam, chlordiazepoxide, cinazepam, cinolazepam, clobazam, clonazepam, clonazolam, clorazepate, clotiazepam, cloxazolam, delorazepam, deschloroetizolam, diazepam, diclazepam, estazolam, ethyl carfluzepate, ethyl loflazepate, etizolam, flualprazolam, flubromazepam, flubromazolam, fluclotizolam, flunitrazepam, flunitrazolam, flurazepam, flutazolam, flutoprazepam, halazepam, ketazolam, loprazolam, lorazepam, lormetazepam, meclonazepam, medazepam, metizolam, mexazolam, midazolam, nifoxipam, nimetazepam, nitemazepam, nitrazepam, nitrazolam, nordiazepam, norflurazepam, oxazepam, phenazepam, pinazepam, prazepam, premazepam, pyrazolam, quazepam, rilmazafone, temazepam, tetrazepam, and triazolam.

In certain embodiments, a patient is administered DMT or a pharmaceutically acceptable salt thereof as described herein along with one or more 5-HT$_{2A}$ specific antagonists and/or inverse agonists. In some embodiments, the patient is administered DMT or a pharmaceutically acceptable salt thereof and the one or more 5-HT$_{2A}$ specific antagonists and/or inverse agonists at the same time. In other embodiments, the patient is administered one or more 5-HT$_{2A}$ specific antagonists and/or inverse agonists prior to DMT or a pharmaceutically acceptable salt thereof administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before DMT or a pharmaceutically acceptable salt thereof administration. In some embodiments, the patient is administered one or more 5-HT$_{2A}$ specific antagonists and/or inverse agonists after DMT or a pharmaceutically acceptable salt thereof administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after DMT or a pharmaceutically acceptable salt thereof administration.

Suitable 5-HT$_{2A}$ antagonists include but are not limited to, trazodone, mirtazapine, metergoline, ketanserin, ritanserin, nefazodone, clozapine, olanzapine, quetiapine, risperidone, asenapine, MDL-100907, cyproheptadine, pizotifen, LY-367,265, 2-alkyl-4-aryl-tetrahydro-pyrimido-azepine, 9-aminomethyl-9,10-dihydroanthracene (AMDA), haloperidol, chlorpromazine, hydroxyzine (atarax), 5-MeO-NBpBrT, niaprazine, altanserin, aripiprazole, etoperidone, setoperone, chlorprothixene, cinaserin, adatanserin, medifoxamine, rauwoiscine, phenoxybenzamine, pruvanserin, deramciclane, nelotanserin, lubazodone, mepiprazole, xylamidine, R-(+)-alpha-(2,3-dimethoxyphenyl)-1-[2-(4-fluorophenethyl)]-4-piperidinemethanol (M100907), mianserin, AT 1015, DV 7028, eplivanserin, 4F 4PP, fanaserin, alpha-phenyl-1-(2- phenylethyl)-4-piperidinemethanol (MDL 1 1, 939), melperone, mesulergine, paliperidone, 1-[2-(3,4-Dihydro-1 I-I-2-benzopyran-1-yl)ethyl]-4-(4-fluorophenyl) piperazine dihydrochloride (PNU 96415E), (2R,4R)-5-[2-[2-[2-(3-methoxyphenyl)ethyl]phenoxy]ethyl]-1-methyl-3-pyrrolidinol (R-96544), sarpogrelate, spiperone, ziprasidone, zotepine, and 7[[4[2-(4-fluorophenyl)ethyl]-1-piperazinylcarbonyl]-1-indole-3-carbonitrile (EMD 281014).

Suitable 5-HT$_{2A}$ reverse agonists include but are not limited to, AC-90179, nelotanserin (APD-125), eplivanserin, pimavanserin (ACP-103), and volinaserin.

In some embodiments, the disclosure provides a method of reducing the negative side effects associated with a traumatic psychedelic experience in a patient undergoing treatment with DMT or a pharmaceutically acceptable salt thereof. In one aspect the method comprising administering to the patient: i) DMT or a pharmaceutically acceptable salt thereof, and ii) one or more 5-HT$_{2A}$ specific antagonists and/or inverse agonists. In another aspect, the method comprising administering to the patient: i) DMT or a pharmaceutically acceptable salt thereof, and ii) one or more cannabinoids or cannabinoid derivatives.

In some embodiments, the cannabinoid is selected from the group consisting of THC (tetrahydrocannabinol), THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin); CBCV (cannabichromevarin); CBGV (cannabigerovarin); CBGM (cannabigerol monomethyl ether); CBE (cannabielsoin); and CBT (cannabicitran). In particular embodiments, the cannabinoid is CBD (cannabidiol).

Dosage regimens may be adjusted to provide the optimum desired response. Treatment dosages may be titrated using routine methods known to those of skill in the art to optimize safety and efficacy.

In a further aspect of the present disclosure, when treating a neuropsychiatric disease or disorder, such as depression (e.g. TRD), anxiety or an addiction, compositions of the present disclosure may be administered in conjunction with psychotherapy, talk therapy, cognitive behavioral therapy, exposure therapy, biofeedback therapy (e.g. EEG-assisted therapy and virtual reality assisted therapy), systematic desensitization, mindfulness, dialectical behavior therapy, interpersonal therapy, eye movement desensitization and reprocessing, social rhythm therapy, acceptance and commitment therapy, family-focused therapy, psychodynamic therapy, light therapy, computer therapy (including digital cognitive behavioral therapy), cognitive remediation, exercise, or other types of therapy such as transcranial magnetic stimulation (TMS). In one embodiment, compositions of the present disclosure may be administered to treat depression in conjunction with digital cognitive behavioral therapy, for example, using the digital program DEPREXIS®. In one embodiment, compositions of the present disclosure may be administered (for example, to treat depression or anxiety) in conjunction with therapy using a transdiagnostic approach (cf. J Consult Clin Psychol. 2020 March; 88(3): 179-195).

All references, articles, publications, patents, patent publications, and patent applications cited herein are incorporated by reference in their entireties for all purposes. However, mention of any reference, article, publication, patent, patent publication, and patent application herein is not, and should not, be taken as acknowledgment or any form of suggestion that they constitute valid prior art or form part of the common general knowledge in any country in the world.

Example 1: DMT Buccal Administration Through Pig Mucosa

| | DMT Buccal Film Composition | | | |
|---|---|---|---|---|
| | | Film Composition | | |
| Formulation | Film #159-78 | | Formulation | |
| Ingredients | (% w/w) | mg/film | (% w/w) | mg/film |
| N,N Dimethyltryptamine | 27.652 | 40.00 | 27.151 | 40.00 |
| Copovidone (Plasdone S-630) | 16.038 | 23.20 | 15.748 | 23.20 |
| Hydroxypropyl Cellulose (Nisso HPC-L) | 32.042 | 46.35 | 31.462 | 46.35 |
| Hydroxypropyl methylcellulose (HPMC E50) | 5.530 | 8.00 | 7.240 | 10.67 |
| Polyethylene glycol 300 | 1.751 | 2.58 | 1.720 | 2.53 |
| L-Glutathione | 1.313 | 1.90 | 1.290 | 1.90 |
| Citric Acid | 8.240 | 11.92 | 8.091 | 11.92 |
| Sucralose | 0.574 | 0.83 | 0.564 | 0.83 |
| Maltitol | 5.530 | 8.00 | 5.430 | 8.00 |
| L-Menthol | 1.327 | 1.92 | 1.303 | 1.92 |
| Methanol | Q.S. | — | Q.S. | — |
| Water | Q.S. | — | Q.S. | — |

Q.S. = Quantity sufficient

Figure 5:
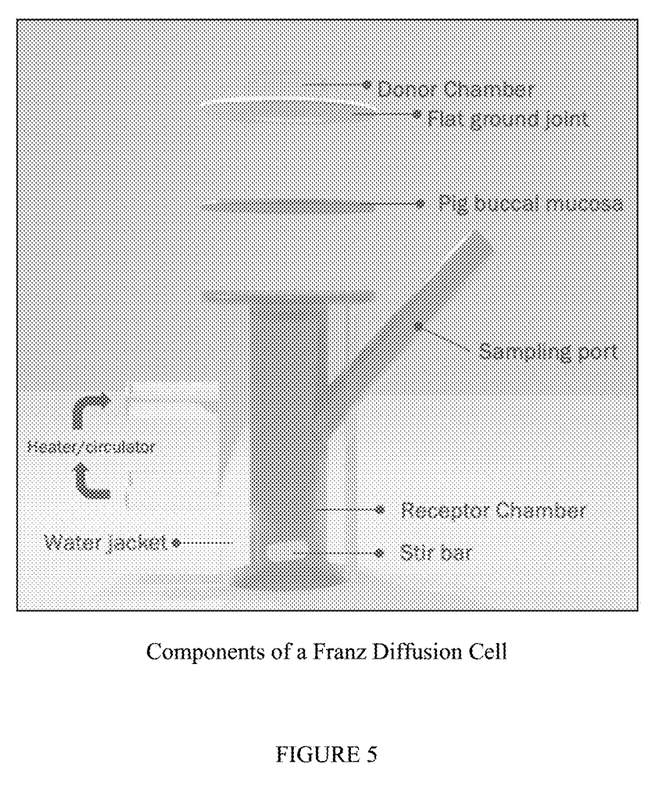
FIG. 5 shows the components of a Franz diffusion cell.

Method:

Permeability of the DMT buccal films were evaluated using a Franz diffusion cell (See FIG. 5).

A buccal film of a specific size was placed in the donor compartment.

M Phosphate Buffer solution of pH 7 was added into the receptor chamber.

Both compartments were separated by a pig buccal mucosa.

The temperature of the receptor medium was maintained at 37±1° C. during the whole study by a circulating water bath and stirred continuously.

Samples of 0.5 mL were withdrawn at predetermined time intervals of over 4 hours and replaced with equal volumes of the medium.

Drug concentrations in the withdrawn samples were analyzed by HPLC.

Results: (See FIGS. 3a and 3b).

Figure 1:
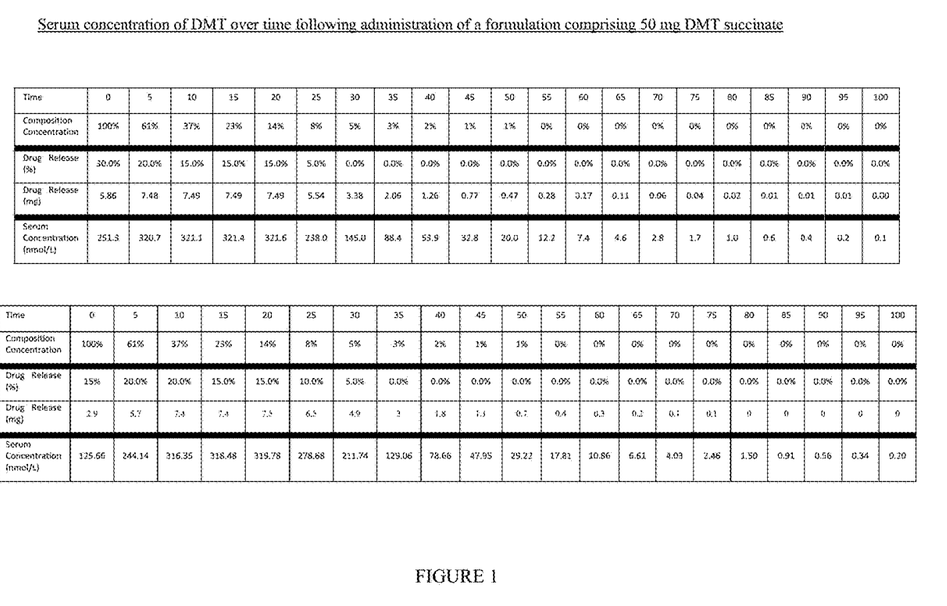
FIG. 1 is a table of the change in DMT concentration in human serum over time following the administration of a pharmaceutical composition of this disclosure including 50 milligrams ("mg") DMT fumarate.
Figure 2:
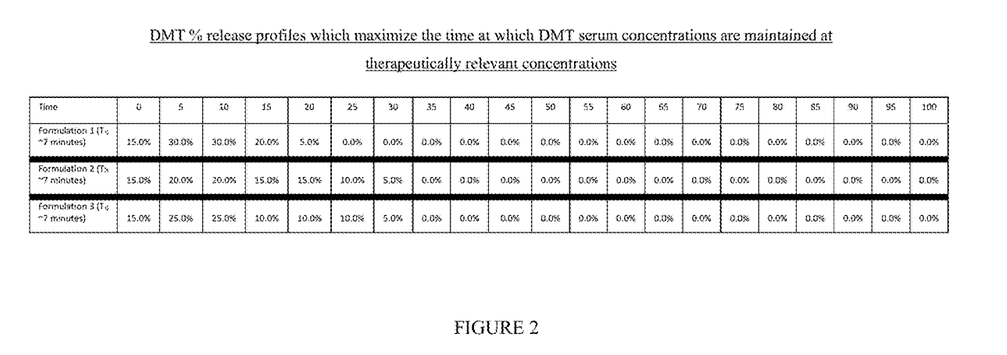
FIG. 2 is a table of the % release of DMT over time in serum following the administration of three different formulations of this disclosure comprising DMT fumarate. Formulations 1, 2 and/or 3 may, for example, be selected from a buccal thin film and a parenteral injection for subcutaneous administration.
Figure 3A:
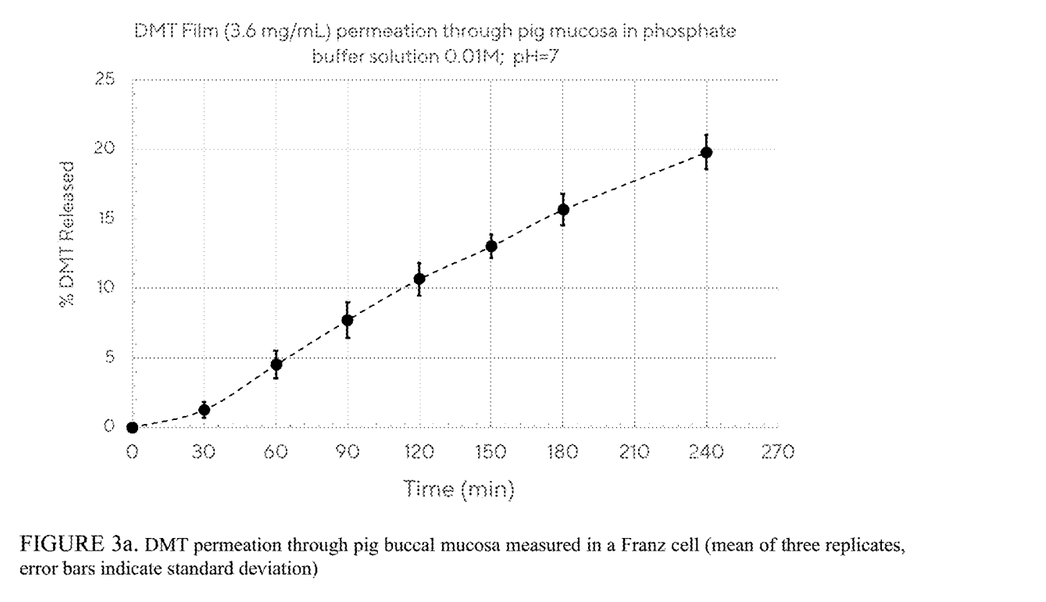
FIG. 3a shows the mean and standard deviation of three replicate measurements of DMT permeation through pig buccal mucosa measured in a Franz diffusion cell.
Figure 3B:
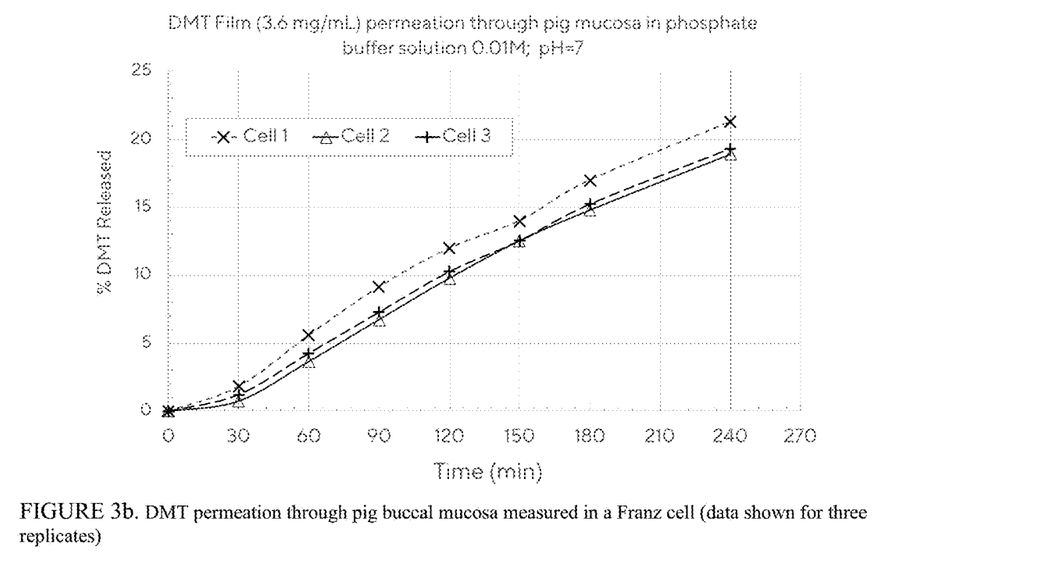
FIG. 3b shows DMT permeability data through pig buccal mucosa measured in a Franz diffusion cell for each of the three replicates.

Permeability of DMT from buccal film was evaluated across the pig buccal mucosa in a 0.01 M phosphate buffer solution of pH 7.

The percent cumulative amount of DMT permeated through the buccal mucosa at different time points is presented.

Based on the DMT permeability profile, a linear increase in permeation of DMT was observed.

The cumulative DMT permeation was found to be about 20% from the finalized buccal film formulation over 4 hours.

Example 2: Study of DMT Succinate Administered Subcutaneously

TABLE 1

DMT plasma concentration parameters on Day 1 following a single SC injection of 5 and 10 mg/kg DMT succinate to rats (males and females combined).

| Analyte | Dose (mg/kg) | Day | $C_{max}$ (ng/mL) | $C_{max}$/Dose (kg * ng/mL/mg) | $T_{max}$ (hr) | $T_{last}$ (hr) | $AUC_{Tlast}$ (hr * ng/mL) | $AUC_{Tlast}$/Dose (hr * kg * ng/mL/mg) | $AUC_{0\text{-}24\ hr}$ (hr * ng/mL) | $AUC_{0\text{-}24\ hr}$/Dose (hr * kg * ng/mL/mg) |
|---|---|---|---|---|---|---|---|---|---|---|
| DMT | 5 | 1 | 228 | 45.5 | 0.5 | 2 | 278 | 55.7 | 306 | 61.1 |
| DMT | 10 | 1 | 1260 | 50.5 | 1 | 8 | 3560 | 142 | 3560 | 143 |

| Time (h) | 5 mg/kg | 10 mg/kg |
|---|---|---|
| 0.5 | 228 | 836 |
| 1 | 202 | 1260 |
| 2 | 27.1 | 1170 |
| 4 | 0 | 149 |
| 8 | 0 | 0.707 |
| 12 | 0 | 0 |
| 24 | 0 | 0 | a: $AUC_{0\text{-}24\ hr}$ not reported due to early termination of Group 8.

Figure 4:
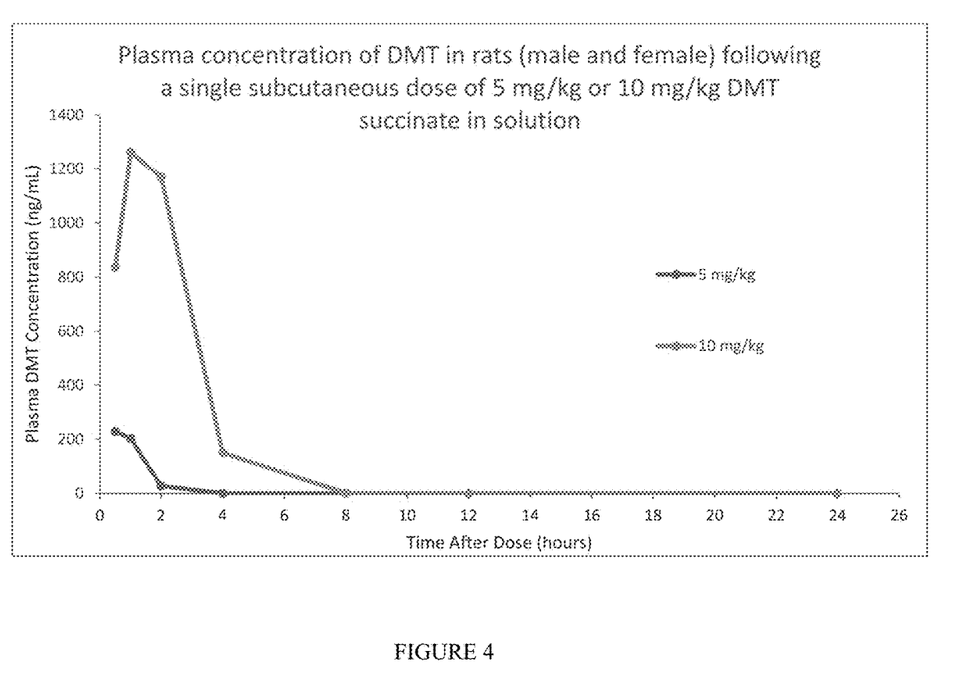
FIG. 4 shows the plasma concentration of DMT in rats following a single subcutaneous dose of 5 mg/kg or 10 mg/kg DMT succinate.

Results are also set forth in FIG. 4.

What is claimed is:

1. A composition comprising (i) an amorphous N,N-dimethyltryptamine (DMT) free base dispersed within a mucoadhesive polymer, wherein said film is capable of releasing DMT so as to maintain a therapeutically effective blood level of DMT for between about 20 and about 60 minutes when administered to a human.

2. The buccal film according to claim 1, exhibiting a therapeutically effective level of DMT for between about 20 and about 45 minutes.

3. The buccal film according to claim 1, exhibiting a therapeutically effective level of DMT for between about 30 and about 45 minutes.

4. The buccal film according to claim 1, exhibiting a therapeutically effective level of DMT for about 45 minutes.

5. The buccal film according to claim 1, having a Tmax less than or equal to 60 minutes.

6. The buccal film according to claim 1, having a Tmax between 5 and 60 minutes.

7. The buccal film according to claim 1, having a Tmax between 8 and 24 minutes.

8. The buccal film according to claim 1, having a Tmax between 10 and 20 minutes.

9. The buccal film according to claim 5, wherein, after Tmax is achieved, the concentration of DMT is maintained at about 50% or more of Cmax for between about 5 minutes to about 60 minutes.

10. The buccal film according to claim 5, wherein, after Tmax is achieved, the concentration of DMT is maintained at about 80% or more of Cmax for between about 5 minutes to about 45 minutes.

11. The buccal film according to claim 10, wherein the concentration of DMT is maintained at about 80% or more of Cmax for between about 10 minutes to about 30 minutes.

12. The buccal film according to claim 2, wherein the concentration of DMT is reduced to about 10% or less of Cmax within about 20 minutes or less.

13. The buccal film according to claim 1, capable of maintaining blood levels of DMT at a concentration of at least about 250 nmol/L for at least about 20 minutes.

14. The buccal film according to claim 1, capable of maintaining blood levels of DMT at a concentration of at least about 250 nmol/L for between about 20 minutes to about 45 minutes.

15. The buccal film according to claim 1, capable of releasing 100% of the DMT from the composition within about 20 minutes following administration to a subject.

16. The buccal film according to claim 1, capable of releasing 100% of the from the composition within about 20 minutes to about 30 minutes following administration to a subject.

17. The buccal film according to claim 1, comprising from about 0.1 mg/kg to about 1 mg/kg of DMT.

18. A method of treating a neurological disease or condition comprising administering to a subject in need thereof a buccal film comprising an effective amount of a N,N-dimethyltryptamine (DMT) free base dispersed within a mucoadhesive polymer, wherein said film is capable of releasing DMT so as to maintain a therapeutically effective blood level of DMT from for between about 20 to about 60 minutes when administered to a human.

19. The method of treatment according to claim 18, wherein the neurological disease or condition is a neuropsychiatric disorder, premenstrual dysphoric disorder, or seasonal affective disorder, anxiety, anxiety disorder, social anxiety disorder, general anxiety disorder (GAD), avolition disorder, bipolar disorder, post-traumatic stress disorder, body dysmorphic disorder, abnormalities of mood or emotion, dysthymia, schizoaffective disorder, schizophrenia a, panic disorder, traumatic stress disorders, phobic disorders, and personality disorders with abnormal mood, addiction, addictive behavior, eating disorder, or pain.

20. The buccal film according to claim 1, capable of maintaining blood levels of DMT at a concentration of at least about 250 nmol/L for between about 20 minutes to about 60 minutes.

21. The buccal film according to claim 1, wherein said polymer film comprises a mucoadhesive polymer.

22. The buccal film according to claim 21, wherein said mucoadhesive polymer comprises cellulose derivatives, polyacrylic acids, polyacrylates, polyethylene oxides, polyvinyl pyrrolidones, polyvinyl alcohols, tragacanth, alginates, gums, soluble starch, gelatin, lectin, pectin, or chitosan.

23. The buccal film according to claim 21, wherein said mucoadhesive polymer comprises a hydrophilic polymer, a polysaccharide, a polysaccharide derivative, or a hydrogel.

24. The buccal film according to claim 21, wherein said mucoadhesive polymer comprises polyacrylic acids, polyacrylates, celluloses, hydroxyalkyl celluloses, polyvinylpyrrolidones, or polyvinyl alcohols.

25. The buccal film according to claim 21, wherein said mucoadhesive polymer comprises Copovidone, hydroxypropyl cellulose, and hydroxypropylmethyl cellulose.

26. The buccal film according to claim 21, wherein said film comprises between about 15% to about 60% of said mucoadhesive polymer.

27. The buccal film according to claim 25, further comprising citric acid.

* * * * *

UNITED STATES PATENT AND TRADEMARK OFFICE
CERTIFICATE OF CORRECTION

Page 1 of 1

| | |
|---|---|
| PATENT NO. | : 11,602,521 B2 |
| APPLICATION NO. | : 17/730013 |
| DATED | : March 14, 2023 |
| INVENTOR(S) | : Srinivas G. Rao et al. |

It is certified that error appears in the above-identified patent and that said Letters Patent is hereby corrected as shown below:

In the Claims

In Claim 1:
At Column 19, Line 54:
"A composition comprising (i) an"
Should read:
-- A buccal film comprising --

In Claim 18:
At Column 20, Line 62:
"amount of a N,N-"
Should read:
-- amount of N,N- --

In Claim 19:
At Column 21, Lines 8 and 9:
"schizophrenia a, panic disorder"
Should read:
-- schizophrenia, panic disorder --

Signed and Sealed this
Twenty-second Day of April, 2025

Coke Morgan Stewart
*Acting Director of the United States Patent and Trademark Office*